United States Patent [19]

Holzner et al.

[11] Patent Number: 5,639,909

[45] Date of Patent: Jun. 17, 1997

[54] PRODUCTION OF 2-PHOSPHONOBUTANE-1, 2,4-TRICARBOXYLIC ACID AND THE ALKALI METAL SALTS THEREOF

[75] Inventors: Christoph Holzner, Köln; Wolfgang Ohlendorf; Hans-Dieter Block, both of Leverkusen; Horst Bertram, Köln; Roland Kleinstück, Bergisch Gladbach; Hans-Heinrich Moretto, Leverkusen, all of Germany

[73] Assignee: Bayer Aktiengesellschaft, Leverkusen, Germany

[21] Appl. No.: 650,681

[22] Filed: May 20, 1996

[30] Foreign Application Priority Data

May 26, 1995 [DE] Germany ............... 19519318.0

[51] Int. Cl.$^6$ ............................................. C07F 9/38
[52] U.S. Cl. ............................................. 562/24
[58] Field of Search ............................................. 562/24

[56] References Cited

U.S. PATENT DOCUMENTS

| 3,886,204 | 5/1975 | Geffers et al. |
| 3,886,205 | 5/1975 | Geffers et al. ............... 562/24 |
| 4,931,586 | 6/1990 | Kleinstruck et al. |

FOREIGN PATENT DOCUMENTS

| 0356880A2 | 3/1990 | European Pat. Off. |
| 0358022A2 | 3/1990 | European Pat. Off. |
| 2061838 | 6/1972 | Germany. |
| 2229087 | 12/1973 | Germany. |
| 2745982 | 4/1979 | Germany. |

OTHER PUBLICATIONS

A.N. Pudovik, Bull. Acad. Sci. USSR, Classe, Sci Chem. pp. 821–824 (1952).

*Primary Examiner*—Johann Richter
*Assistant Examiner*—Michael G. Ambrose
*Attorney, Agent, or Firm*—Spurng Horn Kramer & Woods

[57] ABSTRACT

This invention relates to an improved process for the production of 2-phosphono-butane-1,2,4-tricarboxylic acid (PBTC) and the alkali metal salts thereof, in which process dialkyl phosphite, preferably dimethyl or diethyl phosphite, and ethene-1,2-dicarboxylic acid dialkyl ester, in particular the dimethyl or diethyl ester of maleic acid and/or fumaric acid, are initially reacted in the presence of a basic catalyst to yield a phosphonosuccinic acid tetraalkyl ester, the resultant ester is thereupon reacted without further working up with acrylic acid alkyl ester, preferably methyl or ethyl acrylate, in the presence of an alkaline catalyst and the reaction product obtained in this manner is saponified without further working up to yield PBTC or the alkali metal salts thereof. The product when mixed with bleaching lye exhibits reduced chlorine depletion.

4 Claims, No Drawings

PRODUCTION OF 2-PHOSPHONOBUTANE-1, 2,4-TRICARBOXYLIC ACID AND THE ALKALI METAL SALTS THEREOF

This invention relates to an improved process for the production of 2-phosphono-butane-1,2,4-tricarboxylic acid (PBTC) and the alkali metal salts thereof, in which process dialkyl phosphite, preferably dimethyl or diethyl phosphite, and ethene-1,2-dicarboxylic acid dialkyl ester, in particular the dimethyl or diethyl ester of maleic acid and/or fumaric acid, are initially reacted in the presence of a basic catalyst to yield a phosphonosuccinic acid tetraalkyl ester, the resultant ester is thereupon reacted without further working up with an acrylic acid alkyl ester, preferably methyl or ethyl acrylate, in the presence of an alkaline catalyst and the reaction product obtained in this manner is saponified without further working up to yield PBTC or the alkali metal salts thereof.

It has already been found that phosphonosuccinic acid tetraalkyl esters may be produced in a Michael addition reaction from dialkyl phosphite and maleic acid or fumaric acid dialkyl esters in the presence of alkali metal alkoxides (A. N. Pudovik, Bull. acad. sci. USSR, Classe sci. chim. 1952, pages 821–824). The tetramethyl or tetraethyl phosphonosuccinic acid esters produced in this manner are purified by distillation and obtained at yields of approximately 80%.

DE-A 2 061 838 describes the synthesis of 2-phosphonobutane-1,2,4-tricarboxylic acid by the reaction of equimolar quantities of tetramethyl phosphonosuccinate with methyl acrylate or acrylonitrile in the presence of 100–150 mmol/mol of sodium methanolate as catalyst and subsequent hydrolysis with dilute hydrochloric acid. Distilled tetramethyl phosphonosuccinate is used in this process and volatile secondary products are removed under a vacuum at 80°–90° C. from the intermediate 2-phosphonobutane-1,2,4-tricarboxylic acid pentamethyl ester or 2-dimethyl-phosphono-4-nitrilobutane-1,2-dicarboxylic acid dimethyl ester prior to saponification.

Other prior art saponification processes for 2-phosphonobutane-1,2,4-tricarboxylic acid pentamethyl ester, such as hydrolysis without the addition of catalysts external to the system (DE-A 2 229 087) and hydrolysis under pressure (DE-A 2 745 982), also generally start from pre-purified educts.

Disadvantages of the above-stated methods for the preparation of 2-phosphonobutane-1,2,4-tricarboxylic acid are that it is necessary to purify the phosphonosuccinic acid tetraalkyl ester by distillation as the preceding synthesis yields only a highly impure product. It is also necessary according to the above-stated processes, in order to purify the product, to remove readily volatile constituents by vacuum distillation at a bottom temperature of up to 100° C. before saponification of 2-phosphonobutane-1,2,4-tricarboxylic acid pentaalkyl ester.

EP-A 358 022, on the other hand, describes a process which allows the production of 2-phosphonobutane-1,2,4-tricarboxylic acid (PBTC, industrial grade) or the alkali metal salts thereof in an industrially advantageous, continuous process while avoiding the stated disadvantages, in particular intermediate purification. A disadvantage of this process is, however, that the product (PBTC, industrial grade), when used as a component in cleaning agents containing bleaching lye, decomposes a certain proportion of the bleaching lye ("chlorine depletion"). This disadvantage also affects those products produced using Pudovik's process (see above) and using the process of DE-A 2 061 838, both when intermediate purification is performed at the phosphonosuccinic acid ester stage and when such intermediate purification is dispensed with, indeed, in quantity terms, to a greater extent than the products produced according to EP-A 358 022.

The object is to provide a process which has the advantages of hitherto known processes, but which simultaneously allows the production of a product which exhibits no or less chlorine depletion in the stated application.

It has now surprisingly proved possible to achieve this object by performing the reaction of phosphonosuccinic acid tetraalkyl ester with acrylic acid alkyl ester during synthesis of 2-phosphonobutane-1,2,4-tricarboxylic acid and the salts thereof in batches and not continuously and by maintaining very specific quantity ranges according to the invention of starting materials and other auxiliary substances and very specific temperature ranges according to the invention.

The present invention provides a process for the production of 2-phosphonobutane-1,2,4-tricarboxylic acid (PBTC) or the alkali metal salts thereof by reacting phosphonic acid dialkyl ester with ethene-1,2-dicarboxylic acid dialkyl ester, in which the alkyl groups in both groups of materials are each mutually independently methyl or ethyl groups, in a molar ratio of 1:1 to 1:1.1, preferably of 1:1.03 to 1:1.07, in the presence of alkali metal methylate or ethylate to yield phosphonosuccinic acid tetraalkyl ester and subsequently reacting the reaction product obtained in this manner without a working up or purification stage in a second stage with 0.9–1.1 mols, preferably 1–1.07 mols, of acrylic acid alkyl ester, in which the alkyl groups are methyl or ethyl groups, in the presence of alkali metal methylate or ethylate as catalyst and with the addition of methanol or ethanol to yield 2-phosphono-butane-1,2,4-tricarboxylic acid pentaalkyl ester, in which the alkyl groups are methyl or ethyl groups, and reacting the reaction product obtained in this manner without further working up by means of acid hydrolysis, preferably with PBTC-catalyzed hydrolysis, at 100° to 150° C., preferably at 105°–130° C., which process is characterized in that the second reaction stage, comprising the reaction of phosphonosuccinic acid tetraalkyl ester with acrylic acid alkyl ester, in which the alkyl groups are methyl or ethyl groups, is performed in batches in the presence of 1–2 mols, preferably of approximately 1.5 mols, of methanol or ethanol and in the presence of 5 to 50 mmols, preferably of 10 to 40 mmols, of alkali metal methylate or ethylate, in each case relative to 1 mol of 2-phosphonobutane-1,2,4-tricarboxylic acid to be produced, at temperatures of −20° C. to +50° C., preferably of 0° C. to +25° C., with a residence time of >500 minutes, preferably >700 minutes.

The reaction stages preceeding and following the second reaction stage, i.e. the batchwise reaction of phosphonosuccinic acid tetraalkyl ester with acrylic acid alkyl ester, may be performed both in batches and continuously.

The above-mentioned chlorine depletion is of practical significance as PBTC, under the trade name "BAYHIBIT®AM" (commercial product of Bayer AG), is widely used industrially in industrial cleaning agents containing bleaching lye. 2-Phosphonobutane-1,2,4-tricarboxyclic acid itself is in fact stable with regard to bleaching lye, unlike the phosphonates amino-tris-methylenephosphonic acid (ATMP) and 1-hydroxyethane-1,1-diphosphonic acid (HEDP) which are also used on an industrial scale as sequestrants and incrustation inhibitors. The observed chlorine depletion is thus attributed to the small quantities of impurities contained in industrial grade PBTC. For example, in a cleaning agent prepared from 50% of an industrial grade bleaching lye containing 13.4% $Cl_2$, 10% of a 50% sodium hydroxide solution and 4% of BAYHIBIT®AM (industrial grade PBTC), only 6.4% of chlorine is found once the components have been mixed, instead of the expected 6.7%. In this case, chlorine depletion was 0.3%.

The characteristic of consuming chlorine in an alkaline medium (chlorine depletion) is also unaffected with regard to a reduction in chlorine depletion by distillation whether at the phosphonosuccinic acid tetraalkyl ester stage or at the 2-phosphono-butane-1,2,3-tricarboxylic acid pentaalkyl ester stage, as was performed at considerable expense in the prior, above-stated publications in order to purify the product. This fact is substantiated by the comparative examples herein below.

Surprisingly, the product 2-phosphonobutane-1,2,4-tricarboxylic acid obtained according to the invention is distinguished by dramatically reduced chlorine depletion, which is superior to the products obtained using hitherto known methods even with distillative purification in the intermediate stages and to the products obtained from continuous synthesis (see Comparative Example 3), without any disadvantages with regard to its hardness-stabilising effect.

The process according to the invention allows the desired products, 2-phosphono-butane-1,2,4-tricarboxylic acid or the alkali metal salts thereof, to be obtained in good yields and elevated quality in an industrially straightforward manner without the formation of unwanted secondary products and without using excess reactants or auxiliary substances which subsequently have to be removed. The process according to the invention allows an industrially straightforward synthesis of high quality 2-phosphonobutane-1,2,4-tricarboxylic acid without distillation stages between the individual stages of the synthesis.

A process is thus available which makes it possible to produce PBTC or the salts thereof, which are already widely used as an industrial product under the trade name Bayhibit® (for example as a scale and corrosion inhibitor in cooling water treatment, as an incrustation inhibitor in industrial cleaning agents, as a sequestrant and dispersant) in a simple manner such that chlorine depletion is greatly reduced when it is used together with bleaching lye.

The following examples are intended to illustrate the process according to the invention in greater detail.

EXAMPLE 1

Production of 2-phosphonobutane-1,2,4-tricarboxylic acid

A mixture of 6.81 g of 25% methanolic sodium methylate solution (corresponding to 31.5 mmols of sodium methylate) and 92.43 g of methanol is added dropwise within 20 minutes at 12° C. with stirring and vigorous cooling to a mixture of 508 g (2 mols) of tetramethyl phosphonosuccinate and 189.2 g (2.2 mols) of methyl acrylate. Stirring is then continued for a total of 48 hours at 12° C.

After 48 hours, the reaction mixture is saponified with 1000 ml of 22% hydrochloric acid while being refluxed for 96 hours. The hydrochloric acid and water are then distilled off at 16 mbar until the concentration of the 2-phosphono-butane-1,2,4-tricarboxylic acid (PBTC) present in the bottom has risen to 50% (concentration determined by potentiometric titration with sodium hydroxide solution).

A $^{31}$P-NMR spectrum of the residue exhibits the signals for phosphonosuccinic acid (PBS), monomethyl 2-phosphonobutane-1,2,4-tricarboxylate (MM-PBTC), 2-phosphonobutane-1,2,4-tricarboxylic acid (PBTC) and phosphate with the following signal intensities (area %):

| PBS | 3.6% |
|---|---|
| MM-PBTC | 0.2% |
| PBTC | 95.8% |
| Phosphate | 0.3% |

The Gardner color index (to DIN 53 995) is <1. Chlorine depletion, determined in accordance with the following instructions, is 8 mg of chlorine per g of 50% solution.

Method for measuring chlorine depletion

1. Production of a disinfectant cleaning agent I:

| | Components |
|---|---|
| 370 g | of water (demineralized) |
| 30 g | of 50% PBTC solution |
| 100 g | of 50% sodium hydroxide |
| 500 g | of industrial grade bleaching lye (13–14% $Cl_2$) |

A cleaning agent I is produced from the above-stated components in the following manner:

The water is initially introduced into a 2 l glass, beaker and the PBTC solution and then the sodium hydroxide solution are slowly added with thorough stirring.

Once these components are completely mixed, the bleaching solution is slowly added, again with stirring.

2. Production of a cleaning agent II:

A cleaning agent II similar to cleaning agent I is simultaneously produced, in which an additional 30 g of water are used instead of the PBTC solution.

3. Determination of chlorine depletion

Chlorine depletion may be determined once the cleaning agents have stood for approximately 2 hours.

The active chlorine content of cleaning agents I and II is determined by potentiometric titration with arsenous acid. Chlorine depletion in cleaning agent I is calculated by subtracting the active chlorine content of cleaning agent I from the active chlorine content of cleaning agent II.

If the chlorine depletion in a cleaning agent is related to the initial PBTC concentration (50%), the PBTC chlorine depletion is obtained, for example as mg of chlorine per 1 g of PBTC (50%).

EXAMPLE 2

Production of 2-phosphonobutane-1,2,4-tricarboxylic acid

A mixture of 5.56 g of 25% methanolic sodium methylate solution (corresponding to 25.7 mmol of sodium methylate) and 44.28 g of methanol is added dropwise within 15 minutes at 12° C. with stirring and vigorous cooling to a mixture of 254 g (1 mol) of tetramethyl phosphonosuccinate and 86 g (1 mol) of methyl acrylate. Stirring is then continued for a total of 48 hours at 12° C. The batch is then saponified with 975 g of 22% hydrochloric acid while being refluxed for 96 hours. The mixture is then concentrated in a rotary evaporator until a 50% PBTC solution is obtained.

A $^{31}$P-NMR spectrum of the residue exhibits the signals for phosphonosuccinic acid (PBS), monomethyl 2-phosphonobutane-1,2,4-tricarboxylate (MM-PBTC), 2-phosphonobutane-1,2,4-tricarboxylic acid (PBTC) and phosphate with the following signal intensities (area %):

| | |
|---|---|
| PBS | 6.3% |
| MM-PBTC | 0.2% |
| PBTC | 93.1% |
| Phosphate | 0.3% |

The Gardner color index is <1. Chlorine depletion is 20 mg of chlorine per g of 50% solution.

COMPARATIVE EXAMPLE 1

Batchwise production of 2-phosphonobutane-1,2,4-tricarboxylic acid according to DE-A 20 61 838 with distillation of the 2-phosphonobutane-1,2,4-tricarboxylic acid pentamethyl ester.

64.8 g of 25% methanolic sodium methylate solution, diluted with 30.5 g of methanol (corresponding to 0.3 mol of sodium methylate in 100 ml of methanol) are added dropwise within 70 minutes at 12 to 14° C. with stirring and vigorous cooling to a mixture of 508 g (2 mols) of distilled tetramethyl phosphonosuccinate and 172 g (2 mols) of methyl acrylate). The methanol is removed by vacuum distillation (16 mbar) up to a bottom temperature of 80° C). The 2-phosphonobutane-1-tricarboxylic acid pentamethyl ester is then vacuum distilled (approx. 1 mbar) at up to 200° C.

This distillate (459 g) is refluxed for 96 hours with 1148 g of 22% hydrochloric acid. After cooling, hydrochloric acid and water are distilled off until a 50% PBTC solution is obtained.

A $^{31}$P-NMR spectrum of the residue exhibits the signals for phosphonosuccinic acid (PBS), monomethyl 2-phosphonobutane-1,2,4-tricarboxylate (MM-PBTC), 2-phosphonobutane-1,2,4-tricarboxylic acid (PBTC) and phosphate with the following signal intensities (area %):

| | |
|---|---|
| PBS | 6.1% |
| MM-PBTC | 0.7% |
| PBTC | 90.8% |
| Phosphate | 2.4% |

The Gardner color index is 8. Chlorine depletion is 112 mg of chlorine per g of 50% solution.

COMPARATIVE EXAMPLE 2

Batchwise production of 2-phosphonobutane-1,2,4-tricarboxylic acid according to DE-A 20 61 838

64.8 g of 25% methanolic sodium methylate solution, diluted with 30.5 g of methanol (corresponding to 0.3 mol of sodium methylate in 100 ml of methanol) are added dropwise within 70 minutes at 12° to 14° C. with stirring and vigorous cooling to a mixture of 508 g (2 mols) of distilled tetramethyl phosphonosuccinate and 172 g (2 mols) of methyl acrylate. The methanol is removed by vacuum distillation (16 mbar) up to a bottom temperature of 80° C. The remaining 2-phosphonobutane-1-tricarboxylic acid pentamethyl ester is then saponified by perfusion with steam for 18 hours at a bottom temperature of approximately 120° C.

A $^{31}$P-NMP spectrum of the residue exhibits the signals for phosphonosuccinic acid (PBS), monomethyl 2-phosphonobutane-1,2,4-tricarboxylate (MM-PBTC), 2-phosphonobutane-1,2,4-tricarboxylic acid (PBTC) and phosphate in the ratio of the following signal intensities (area %).

PBS: MM-PBTC: PBTC: phosphate=5.6: 0.2: 91.7: 2.5

The Gardner color index is 1.

Chlorine depletion is 100 mg of chlorine per g of 50% solution.

COMPARATIVE EXAMPLE 3 (corresponding to EP-A 0 358 022)

In a continuous reaction, 110 g (1.00 mol) of dimethyl phosphite and 150 g (1.04 mols) of dimethyl maleate are reacted in a first stage at 30° C. with 2.0 g (0.009 g) of a 25% solution of sodium methylate in methanol with thorough stirring and cooling. The average residence time is 3 h 15 min.

This reaction mixture passes into a second reaction stage where it is continuously reacted at 10° C. with 88 g (1.02 mols) of methyl acrylate, 15 g (0.07 mols) of a 25% solution of sodium methylate in methanol and 20 g of methanol with stirring and cooling. The average residence time is 3 h.

The crude ester obtained in this manner is saponified at 100° to 130° C. with intrinsic catalysis over a residence time of 15 h.

A $^{31}$P-NMR spectrum of the residue exhibits the signals for phosphonosuccinic acid (PBS), monomethyl 2-phosphonobutane-1,2,4-tricarboxylate (MM-PBTC), 2-phosphonobutane-1,2,4-tricarboxylic acid (PBTC) and phosphate in the ratio of the following signal intensities (area %).

PBS: MM-PBTC: PBTC: phosphate=4.0: 4.8: 91.0: 0.2

The Gardner color index is <1.

Chlorine depletion is 70 mg of chlorine per g of 50% solution.

It will be appreciated that the instant specification and the claims are set forth by way of illustration and not limitation, and that various modifications and changes may be made without departing from the spirit and scope of the present invention.

We claim:

1. A process for the production of 2-phosphonobutane-1,2,4-tricarboxylic acid (PBTC) or the alkali metal salts thereof comprising a) reacting a phosphonic acid dialkyl ester with an ethene-1,2-dicarboxylic acid dialkyl ester, in which the alkyl groups in both groups of materials are each mutually independently methyl or ethyl groups, in a molar ratio of 1:1 to 1:1.1, in the presence of an alkali metal methylate or ethylate to yield a phosphonosuccinic acid tetraalkyl ester, b) subsequently reacting the reaction product obtained in (a), without a working up or purification stage, with 0.9–1.1 mols of an acrylic acid methyl or ethyl ester in the presence of an alkali metal methylate or ethylate as catalyst and with the addition of methanol or ethanol to yield a 2-phosphonobutane-1,2,4-tricarboxylic acid pentaalkyl ester, the reaction being performed in batches at a temperature of −20° C. to +50° C. with a residence time of >500 minutes, 1–2 tools of the methanol or ethanol and 5 to 50 mmol of the alkali metal methylate or ethylate being employed per mol of 2-phosphonobutane-1,2,4-tricarboxylic acid to be produced, and c) subjecting the reaction product obtained in (b) without further working up to acid hydrolysis at 100°–150° C.

2. A process according to claim 1, wherein in the molar ratio of phosphonic acid dialkyl ester to ethene-1,2-dicarboxylic acid dialkyl ester is from 1:1.03 to 1:1.07.

3. A process according to claim 1, wherein in 1 to 1.07 mols of an acrylic acid methyl or ethyl ester are reacted in the presence of approximately 1.5 tools of methanol or ethanol and 10 to 40 mmol of alkali metal methylate or ethylate at a temperature of 0° C. to 25° C. with a residence time of >700 minutes.

4. A process according to claim 1, wherein in the hydrolysis is catalyzed by 2-phosphonobutane-1,2,4-tricarboxylic acid at 105°–130° C.

\* \* \* \* \*

UNITED STATES PATENT AND TRADEMARK OFFICE
CERTIFICATE OF CORRECTION

PATENT NO. : 5,639,909
DATED : June 17, 1997
INVENTOR(S) : Holzner, et al.

It is certified that error appears in the above-indentified patent and that said Letters Patent is hereby corrected as shown below:

Col. 6, line 65    After " 1-2 " delete " tools " and substitute -- mols --

Col. 8, line 1    After " 1.5 " delete " tools " and substitute -- mols --

Signed and Sealed this

Twenty-eighth Day of April, 1998

*Attest:*

BRUCE LEHMAN

*Attesting Officer*    *Commissioner of Patents and Trademarks*